United States Patent [19]

Fountain et al.

[11] Patent Number: 4,625,730
[45] Date of Patent: Dec. 2, 1986

[54] PATIENT ECG RECORDING CONTROL FOR AN AUTOMATIC IMPLANTABLE DEFIBRILLATOR

[75] Inventors: Glen H. Fountain, Silver Spring; David G. Lee, Jr., Columbia; David A. Kitchin, Seabrook, all of Md.

[73] Assignee: The Johns Hopkins University, Baltimore, Md.

[21] Appl. No.: 721,464

[22] Filed: Apr. 9, 1985

[51] Int. Cl.[4] ............................................. A61N 1/32
[52] U.S. Cl. ................................. 128/419 D; 128/903
[58] Field of Search .................... 128/419 D, 903, 706

[56] References Cited

U.S. PATENT DOCUMENTS

| | | | |
|---|---|---|---|
| 4,223,678 | 9/1980 | Langer et al. | 128/419 D |
| 4,250,888 | 2/1981 | Grosskopf | 128/706 |
| 4,295,474 | 10/1981 | Fischell | 128/419 D |
| 4,407,288 | 10/1983 | Langer et al. | 128/419 D |
| 4,545,030 | 10/1985 | Kitchin . | |

OTHER PUBLICATIONS

Programmable Implantable Medication System (PIMS) Transceiver, A. F. Hogrefe et al., Proceedings of the 7th International Symposium on Biotelemetry, Aug. 15-20, 1982, Stanford, California, pp. 5-8.

Primary Examiner—William E. Kamm
Attorney, Agent, or Firm—Robert C. Kain

[57] ABSTRACT

An implantable automatic defibrillator includes sensors which are placed on or near the patient's heart to detect electrical signals indicative of the physiology of the heart. The signals are digitally converted and stored into a FIFO region of a RAM by operation of a direct memory access (DMA) controller. The DMA controller operates transparently with respect to the microprocessor which is part of the defibrillator. The implantable defibrillator includes a telemetry communications circuit for sending data outbound from the defibrillator to an external device (either a patient controller or a physician's console or other) and a receiver for sensing at least an externally generated patient ECG recording command signal. The patient recording command signal is generated by the hand held patient controller. Upon detection of the patient ECG recording command, DMA copies the contents of the FIFO into a specific region of the RAM.

6 Claims, 6 Drawing Figures

FIG. 4.
GO TO SLEEP LOGIC

PATIENT ECG RECORDING CONTROL FOR AN AUTOMATIC IMPLANTABLE DEFIBRILLATOR

The invention described herein was made in the performance of work under NASA Contract NDPR S-63742-B and is subject to the provisions of Section 305 of the National Aeronautics and Space Act of 1958 (72 Stat. 435; 42 U.S.C. 2457).

BACKGROUND OF THE INVENTION

This invention relates generally to a hand held, patient actuated controller which commands an automatic implantable defibrillator to record electrocardiogram (ECG) signals representing the patient's heart physiology recently detected over a predetermined time period.

Automatic defibrillators are implanted within patients to monitor the electrical activity of the heart of the patient. The automatic defibrillator continuously monitors the heart's activity and determines whether certain arrhythmic events occur, e.g., ventricular fibrillation, ventricular tachycardia, atrial fibrillation, asystole, etc. Upon detecting one of the cardiac events, the automatic defibrillator provides appropriate cardioversion therapy via electrical pacing pulses to the heart and/or a countershock to the heart as programmably established in the defibrillator by the patient's physician. The implantable automatic defibrillator includes a microprocessor and associated digital components such as random access memories (RAMs) and read only memories (ROMs) to carry out these functions.

U.S. Pat. No. 4,407,288 by Langer et al. discloses a programmable, microprocessor based implantable defibrillator; the patent is incorporated herein by reference thereto. The patent discloses the use of two microprocessors, one high speed processor and another low power, low speed processor and discloses a scheme for recording ECG data. To determine whether a predetermined event has occurred, the ECG data is loaded into a precursor memory via a direct memory access (DMA) operation. The low power microprocessor monitors the ECG data in the precursor memory and a dedicated cardiac state evaluation circuit detects the presence of an event, such as an arrhythmia, and then generates appropriate signals directed towards the low power microprocessor. In the absence of signals indicating the occurrence of a predetermined event, the high powered microprocessor is "asleep." When an event is detected, the ECG data in the precursor memory is automatically "frozen" therein and the high speed microprocessor is "awakened" to pass programmable cardioversion commands to other circuitry in the automatic defibrillator. A mechanism is also described in the patent for outputting the ECG data from the precursor memory.

U S. Pat. No. 4,295,474 by Fischell discloses a recorder for an automatic implantable defibrillator; the patent is incorporated herein by reference thereto. The most recently detected ECG data is stored or recorded in a precusor section of a RAM. If an event occurs, a second continuous recording of ECG data is started in the larger portion of the memory; however, further recording or writing of ECG data into the precusor section or the recorded portions of the RAM is inhibited until the contents of the RAM is read out via a telemetry communication link to a physician's console. The physician analyzes the ECG data stored in the precursor memory section immediately preceding the defibrillation activity and stored in the recorded portions of the RAM during the defibrillation episode. Even if no fibrillation episodes (detected cardiac events) have occurred since the patient's last visit to the physician, the physician may place a control command coil or magnet over the implantable defibrillator to instruct the defibrillator to record approximately 70 seconds of current patient ECG data and then immediately transmit that ECG data to the physician's console via a telemetry communication link.

U.S. Pat. No. 4,223,678 by Langer et al. discloses an arrhythmia recorder as part of an implantable defibrillator. In this patent, the ECG data is converted from analog into digital and stored in a first in, first out (FIFO) auxiliary memory. When a fibrillation event is detected, the auxiliary memory is disabled such that no further ECG data is recorded therein and a main memory is actuated to record ECG data during the defibrillation episode. Thereafter, no further ECG data is recorded in the auxiliary memory and the main memory until the physician sends an appropriate command, via a command console, to transmit the ECG data from the auxiliary memory and the main memory to the console by way of a telemetry communication link.

The above noted patents do not discuss a hand held patient record controller which is actuable by the patient and which commands the implantable defibrillator to record the current ECG data.

Because there is a need to establish electronic parameters in the arrhythmia or event detector to properly detect varying degrees of cardiac activity, particularly when microprocessor based defibrillators are capable of distinguishing numerous types of events, it is desirous to record the ECG signals since the detector parameters vary slightly from patient to patient. Also, the defibrillators now provide a plurality of pacing modes to be delivered to the heart dependent upon the type of event. The pacing mode programmed by the physician is dependent upon the previously gathered ECG data by the physician. The greater number of treatment modes generally requires greater number of parameter settings because the physician can establish parameters for the arrhythmia detector and values for the identification of the type of event by the microprocessor which triggers the delivery of a prescribed treatment to the heart. By increasing the modes of treatment, the establishment of parameters to trigger a particular mode is further complicated.

The patient is in a good position to identify the onset of any particular cardiac event, e.g., an arrhythmia. If the parameters in the automatic implantable defibrillator are properly set, the defibrillator will respond, notwithstanding the patient's concern, with the appropriate mode of treatment and record the ECG data. However, if the parameters have been set incorrectly, the defibrillator will not recognize the arrhythmia and hence will not apply any treatment but further will not record the ECG data. In the absence of an ECG recording, the defibrillator cannot be "fine tuned" for a patient's particular requirements. Therefore, a simple, hand held, patient ECG record controller allows the patient to command the implantable defibrillator to record a predetermined amount of recently monitored ECG data whenever the patient feels the onset of a cardiac event.

OBJECTS OF THE INVENTION

It is an object of the present invention to provide a simple, hand held patient ECG record controller for an automatic implantable defibrillator.

It is a further object of the present invention to store or record ECG data as requested by the patient to determine false negatives.

It is an additional object of the present invention to store ECG data detected over a recent time period in a permanent storage region of a RAM without corruption of the current sensing of the ECG data and without corruption of the recently acquired and stored ECG data.

SUMMARY OF THE INVENTION

An implantable automatic defibrillator includes sensors which are placed on or near the patient's heart to detect electrical signals indicative of the physiology of the heart. A digital data compression circuit in the implantable body of the defibrillator converts the sensed ECG signals into digital data representative of those signals. In one embodiment, a direct memory access (DMA) controller continually transfers and stores the compressed digital signals in a FIFO region of a RAM. The DMA controller operates transparently with respect to a microprocessor which is part of the defibrillator. When a heart arrhythmia is detected, an event signal command is generated by a detection circuit. The microprocessor identifies the arrhythmia and, if appropriate, begins one of several programmable treatment modes stored in a ROM. The implantable defibrillator includes a telemetry communications circuit for sending data outbound from the defibrillator to an external device (e.g., a patient controller or a physician's console) and a receiver for sensing at least an externally generated patient ECG recording command signal (from the patient controller). The microprocessor recognizes the patient record command and further recognizes the event signal command and directs the DMA to copy the previously stored digital signals in the FIFO region of the RAM into a "permanent" storage region of the RAM. The RAM is divided into different regions, one region for recording the ECG data dependent upon the receipt of the patient record command and other regions for storing ECG data upon identification of a cardiac event. Further, the microprocessor includes means for actuating the transmitter to effect the outbound transmission of data from the RAM.

BRIEF DESCRIPTION OF THE DRAWINGS

The subject matter which is regarded as the invention is particularly pointed out and distinctly claimed in the concluding portion of the specification. The invention, however, together with further objects and advantages thereof, may best be understood by reference to the following description taken in connection with the accompanying drawings in which:

DETAILED DESCRIPTION OF THE INVENTION

This invention relates to an automatic implantable defibrillator which records or stores ECG data dependent, in part, on a patient ECG record controller.

Figure 1:
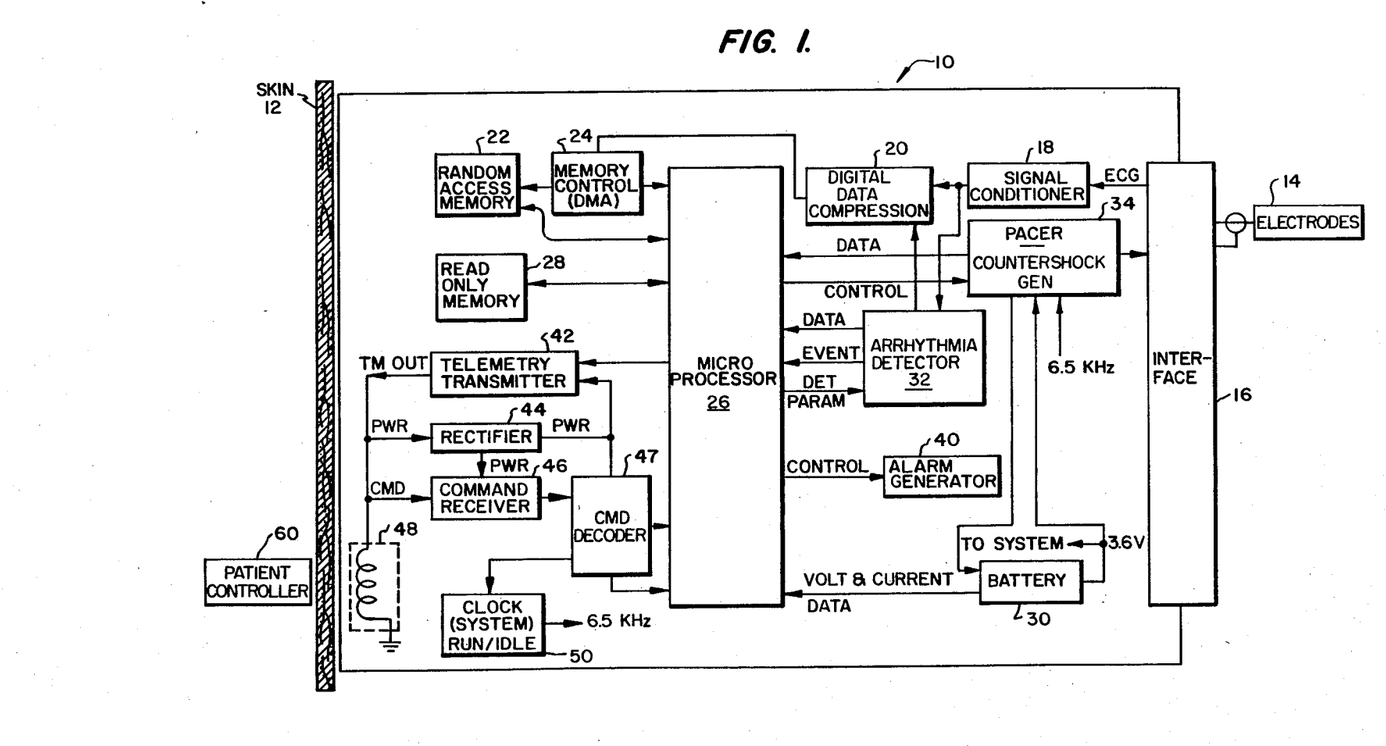
FIG. 1 is a functional block diagram of the automatic implantable defibrillator.

FIG. 1 illustrates, schematically, an automatic implantable defibrillator 10 surgically implanted beneath the skin 12 of a patient. Electrodes 14 may include atrial and ventricular bipolar electrodes and transcardiac patch electrodes. U.S. patent application Ser. No. 478,038, filed Mar. 23, 1983, and assigned to the assignee of the present invention, describes bipolar electrodes. Generally, electrodes 14 are placed on or in the proximity of the patient's heart (not shown) to detect electrical signals indicative of the physiology of the heart. Hereinafter, such electrical signals are referred to as electrocardiogram signals or ECG signals or data.

An electronic interface 16 couples the encased defibrillator 10 with electrodes 14. Interface 16 links the implanted electrodes 14 to the implanted defibrillator 10. As recognized by persons of ordinary skill in the art, defibrillator 10 is encased in a container (not shown) which hermetically seals the components of the defibrillator from the patient's bodily fluids. Generally, interface 16 protects the electronic components from voltage induced by the heart after application of countershock pulses from the defibrillator or protects the electronics from any externally applied electric potential.

The analog ECG signals are applied to signal conditioner 18 which amplifies the ECG waveform to a level complementary to the balance of the electronic components. The conditioned ECG signal is applied to a digital data compression circuit 20 which generates a digital sequence of bits for storage in the FIFO. In one embodiment, the data compression circuit uses delta modulation as described in U.S. patent application Ser. No. 502,499, filed June 9, 1983, assigned to the assignee of the present invention; the patent application is incorporated herein by reference thereto. The digital data compression circuit 20 converts the conditioned, analog ECG signal into digital signals representative of the physiology of the patient's heart.

The digital signals from compression circuit 20 are stored in a FIFO region in RAM 22 by operation of DMA memory control 24. As will be described later, DMA control 24 operates transparently with respect to the operation of microprocessor 26. As shown in FIG. 1, microprocessor 26 also has access to RAM 22.

In one embodiment, microprocessor 26 is an RCA 1802. The microprocessor executes a plurality of instruction sets or programs stored in ROM 28.

Arrhythmia detector 32 continuously monitors the flow of ECG data through signal conditioner circuit 18 and generates an event command signal which is recognized by microprocessor 26. In one embodiment, arrhythmia detector 32 generates the following information which is accessible by the microprocessor: period of each R—R interval; period of each P—P interval; the integrated probability density function count; the R wave peak; P wave peak; declaration of an asystole; and notification of a non-physiologic heart rate. Functionally, arrhythmia detector 32 tests this information and other ECG data against pre-programmed parameters or thresholds and notifies the microprocessor of the occurrence of each cardiac event. As stated earlier, defibrillator 10 is programmable such that the physician establishes parameters that are appropriate for the given patient, to trigger the delivery of modes of treatment such as pacing pulses or countershocks to the patient's heart. Therefore, microprocessor 26 sets some threshold detection parameters within arrhythmia detector 32. As will be described later, microprocessor 26 is "asleep" or temporarily disabled in the absence of abnormal cardiac activity, communications link or other component interrupts, but arrhythmia detector 32 continuously monitors flow of ECG data passing through the signal conditioner circuit 18.

After a predetermined event is detected by arrhythmia detector 32, the microprocessor is awakened and begins execution of programs or instruction sets stored in ROM 28. In one embodiment, microprocessor 26 further determines or confirms the presence of cardiac event and the significance of that event. If necessary, microprocessor 26 commands pacer/countershock generator 34 to deliver pacing pulses or countershocks, via interface 16 and electrodes 14, to the heart. The pacer/countershock generator 34 passes to microprocessor 26 various information on the illustrated data line. As is recognized by persons of ordinary skill in the art, the countershock generator is coupled to a battery 30 because the generator includes a capacitor which must be charged prior to the delivery of the countershock to the patient's heart.

Microprocessor 26 also controls alarm generator 40 which provides, in one embodiment, a sonic alarm to alert the patient of the following items: a deteriorating battery level; the application of an external magnet control; when the event history table is filled or the ECG RAM recording regions are full.

The telemetry communications portion of defibrillator 10 includes telemetry transmitter 42, rectifier 44, command receiver 46, command decoder 47 and transmission coil 48. A clock system run/idle circuit 50 is coupled to one of the outputs of command decoder 47. A patient controller 60 communicates with the telemetry communications section of defibrillator 10 through skin 12 and the casing, not shown, surrounding defibrillator 10.

Figure 2:
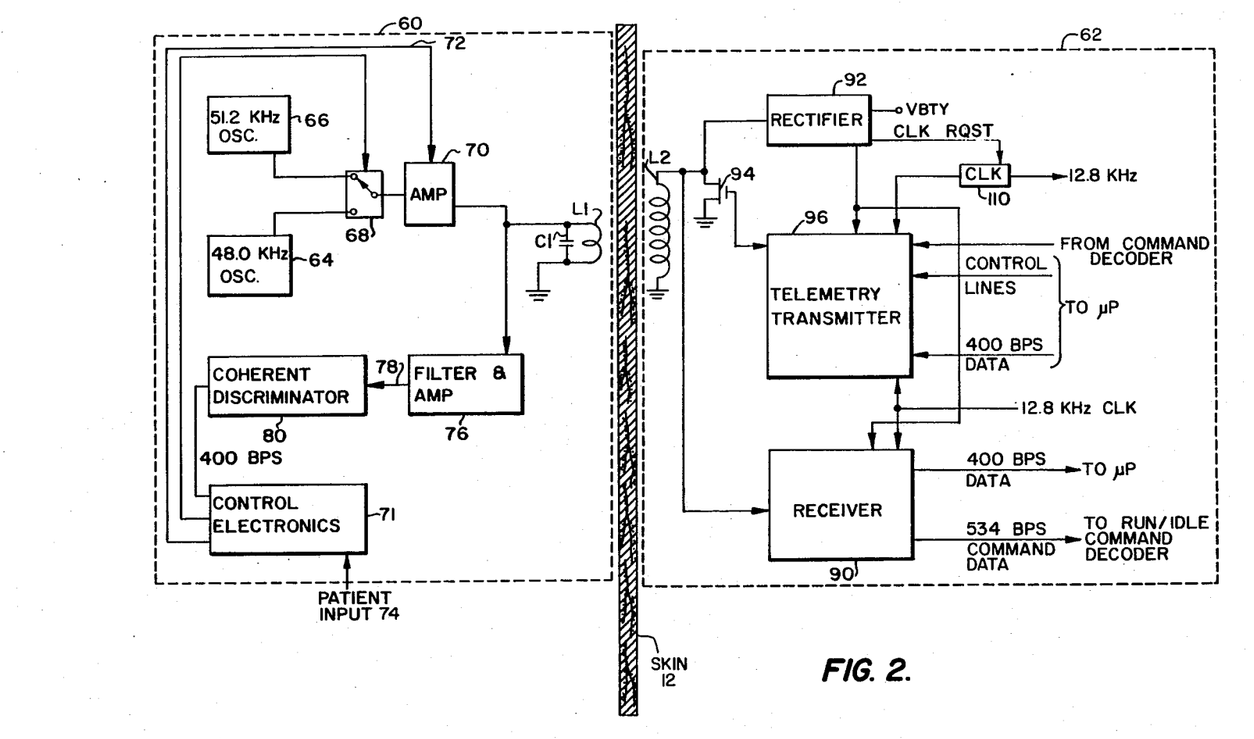
FIG. 2 is a detailed functional diagram of the patient controller and the communications section of the implantable defibrillator.

FIG. 2 illustrates a detailed functional schematic of the communications section 62 of the defibrillator and the detailed functional schematic of patient controller 60 external to skin 12 of the patient. In one embodiment, coil L1 and capacitor C1 comprise a resonant circuit having a central frequency located approximately at the median frequency (on a logrithmic scale) between 51.2 kHz and 48.0 kHz. Coil L1 is a three inch diameter coil which is excited with a 30-volt peak to peak drive voltage. An inductive link is established between coil L1 in patient controller 60 and coil L2 in communications section 62 of the defibrillator. Coil L2 is a 200 turn coil which allows establishment of the inductive communications link at approximately a range of up to three inches. Patient controller 60 emits a frequency shift keyed (FSK) field generated at 48.0 or 51.2 kHz. Oscillators 64 and 66 are switchably coupled via control switch 68 to amplifier 70. In one embodiment, amplifier 70 is a power driver class C amplifier generating the 30 volts peak to peak for the resonant circuit L1, C1. A battery or power source is not shown in patient controller 60 but some type of power source is necessary for the circuitry.

Switch 68 is controlled by control electronics 70 which actuates the switch to apply either the 51.2 kHz or the 48.0 kHz FSK signal to the resonant circuit L1, C1. Line 72 coupling control electronics 71 to amplifier 70 establishes the mark bit for the inbound synchronous data transmission from patient controller 60 to communication section 62 of the defibrillator. The designations "inbound" and "outbound" communications data flow are taken from the perspective of the implantable defibrillator. Control electronics 71 is actuated by patient input 74 which could be a pushbutton or any easily operated patient actuated device.

The outbound data transmission is detected by resonant circuit L1, C1 and a filter and amplifier circuit 76 filters out the carrier frequency from the signal sent by communication section 62. As will be described later, that outbound data transmission is amplitude modulated (AM) at a 51.2 kHz frequency. Filter and amplifier 76 produce a square wave on line 78 which is fed to coherent discriminator 80 (similar in nature to an envelope detector) which generates a serial data bit stream at 400 bps (400 bits per second).

If the occasion arises that the patient feels a cardiac event is occurring, the patient brings controller 60 to within 3 inches of the implanted defibrillator. After actuation of patient input 74, control electronics 71 transmits an FSK signal at 534 bps which is designated the telemetry mode or TM signal. Patient controller 60 initially sends a bit mark by turning off amplifier 70 to signify the beginning of the synchronous data communication session. Thereafter, switch 68 is actuated at a rate corresponding to 534 bps and the FSK signal is inductively picked up by coil L2. In communications section 62, coil L2 is coupled to receiver 90 and rectifier 92 and CMOS transistor 94. Rectifier 92 converts the energy in coil L2 and supplies power to the telemetry transmitter 96 and receiver 90. Therefore, the energy transmitted via the inductive link between resonant circuit L1, C1 and coil L2 is utilized to power substantially all of the components in communications section 62 of the defibrillator. Rectifier 92 also generates a clock request for clock 110 to apply clocking pulse to the transmitter and to the receiver during the communications session.

After the mark bit in the telemetry TM mode, patient controller 60 sends a request status signal to communications section 62 inquiring about the status of the defibrillator, i.e., is the defibrillator in a "run" mode or in a "idle" mode? The run mode signifies defibrillator 10 is operating by continuously detecting and monitoring ECG data. In contrast, the idle mode occurs when defibrillator 10 is "off" or in a "shelf state" wherein the ECG data is not being continuously monitored. As is recognized by persons of ordinary skill in the art, defibrillator 10 can be programmed to automatically revert to the idle mode when a fault occurs either in the software, hardware or firmware of the device.

Receiver 90 is a digital discriminator which primarily counts zero crossings of the carrier signal to decode the data obtained via coil L2. The high speed data 534 bps stream is applied to the run/idle command decoder which is functionally illustrated as command decoder 47 in FIG. 1 and is associated with clock run/idle circuit 50 in that Figure. Although FIG. 2 shows the 400 bps data line coupled to the microprocessor and the 534 bps data line coupled to the run/idle command decoder, it is recognized that command decoder 47 in FIG. 1 essentially applies the slower data stream to a data bus tied to the microprocessor (see FIG. 3) and independently decodes or processes the higher speed data. The command decoder transparently operates on the higher speed data with respect to the balance of the defibrillator circuitry. Therefore, the run/idle command decoder is not significantly affected by the operation of microprocessor 26 and other associated circuitry and acts as the ultimate "on/off" switch for the implantable device.

The command decoder responds to the request status signal by sending the appropriate return TM code signal via telemetry transmitter 96 by shorting out transistor 94 and changing the inductive field between coils L1 and L2. This change of the inductive coupling between the coils provides an amplitude modulated signal at the particular frequency exciting coil L1. When controller 60 is not transmitting, the excitation frequency of 51.2 kHz from oscillator 66 is applied to coil L1. When patient controller 60 detects the return status TM signal from communications section 62, control electronics 71 then shifts into the slower transmission bit rate of 400 bps by sending a stop TM command at the 537 bps volts. Substantially simultaneously to this operation within communications section 62 of the status data, microprocessor 26 is awakened if the microprocessor has been asleep as will be described later.

Control electronics 71 in patient controller 60 then transmits at 400 bps a message formatted as follows:

---

$FF_H$... provides freq. sync. for subcarrier
$AA_H$... synchronization character and bit sync.
Message body length minus one
Message body
.
.
.
Longitudinal parity

---

To insure that a particular patient controller only interacts with a specific defibrillator, the controller sends a special command or device code signal unique to both the controller and the defibrillator. The device code can be part of or can be separate from the patient ECG record command in the message body.

The length of the message body, sent inbound to defibrillator 10, is limited to 32 bytes. As will be described later, each byte of data received defibrillator 10 is parity checked (lateral check) and each complete message block is longitudinally parity checked to ensure the integrity of the data transmission. As is recognized by persons of ordinary skill in the art, command decoder 47 in FIG. 1 could include certain control registers, and data registers and comparators which would check for the presence of the device code. Alternatively, this type of code check could be accomplished by microprocessor 26 executing certain programs in ROM 28 upon detection of the establishment of a communications link. It should be appreciated that the integrity of the data transmission is critical since faulty transmission or an improper association between one type of patient controller with another type of defibrillator could result in the failure of the defibrillator to record the recently acquired ECG data in RAM 22.

Figure 3:
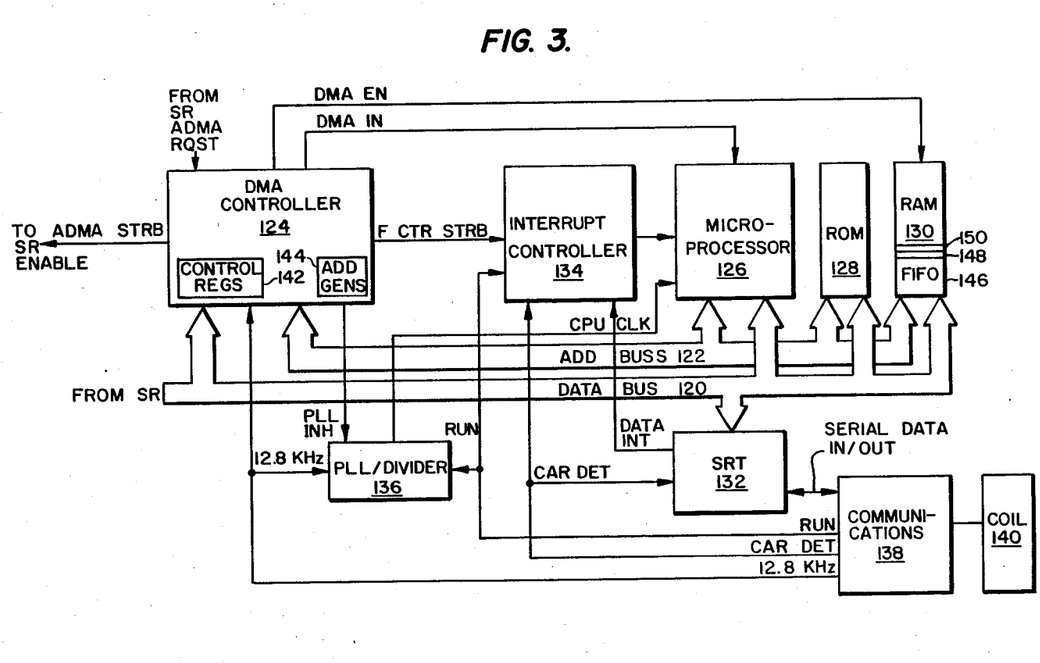
FIG. 3 is a logic block diagram of a portion of the defibrillator showing among other things the DMA controller, the microprocessor, ROM, and RAM.

FIG. 3 is a logic level functional diagram showing the various components utilized in the defibrillator to record or store the ECG data. Data bus 120 and address bus 122 link DMA controller 124, microprocessor 126, ROM 128, and RAM 130. A synchronous receiver transmitter (SRT) 132 is coupled to data bus 120. Interrupt controller 134 prioritizes the various interrupts generated in the defibrillator and notifies microprocessor 126 accordingly. Phase lock loop (PLL)/divider 136 is utilized to generate various clocking pulses and is also utilized to put the microprocessor 126 to sleep as will be discussed later. Communications block 138 is coupled to coil board 140 and both generally correspond to communications section 62 discussed above with respect to FIG. 2. As recognized by persons of ordinary skill in the art, FIG. 3 is a greatly simplified logic diagram of this system. Only the major components and the important interconnections therebetween are identified to enable one of ordinary skill in the art to practice the present invention. For example, DMA controller 124 includes control registers 142 and address generators 144 which facilitate the transfer of ECG data from the digital data compression circuit 20 (FIG. 1) into the FIFO region 146 of RAM 130 (FIG. 2) The control registers 142 in DMA controller 124 monitor the ECG data transfer, whereas the address generators identify the storage locations in the RAM. Also, address generators 144 and control registers 142 facilitate the transfer of data from FIFO region 146 into permanent memory regions 148 or 150 as prescribed by microprocessor 126.

DMA controller 124 includes a register holding the DMA controller control word: DMAC(W), and another register holding the DMA controller status word: DMAS(R).

| DMA Controller Control Word DMAC(W) | |
|---|---|
| Bits | Function |
| 0-3 | Number of blocks to be transferred. |
| 4 | Set to latch FIFO pointer. Cleared by hardware. |
| 5 | Set to request transfer of parameters for pacing unit. |
| 6 | Set to clear the transfer completed bit in the DMAS. Cleared by hardware. |
| 7 | Set to enable loading of number of blocks to be transferred (bits 0-3 above). Cleared by the microprocessor. |

| DMA Controller Status Word DMAS(R) | |
|---|---|
| Bits | Function |
| 0-3 | Number of blocks remaining to transfer. |
| 4 | Set to indicate FIFO pointers are equal. |
| 5 | Echoes bit 5 in DMAC. |
| 6 | Set to indicate completion of FIFO transfer. Cleared by microprocessor. |
| 7 | Echoes bit 7 in DMAC. |

The digital data compression circuit 20 includes a shift register (designated SR in FIG. 3) which is loaded with the compressed ECG digital data. This shift register may be characterized as a DMA port. When the shift register is full with a byte of ECG data, the register generates an ADMA request (ADMA RQST) signal.

At this point, a discussion of the two modes of operation of microprocessor 126, e.g., awake and asleep, is necessary. To reduce the power requirements of the defibrillator, microprocessor 126 is put asleep such that the microprocessor only draws quiescent power from the battery 30 in defibrillator 10. U.S. Pat. No. 4,545,030, entitled "Synchronous Clock Stopper for Microprocessor" and assigned to the assignee of the present invention, discusses in detail the asleep and awake modes for the microprocessor; the patent is incorporated herein by reference thereto.

Figure 4:
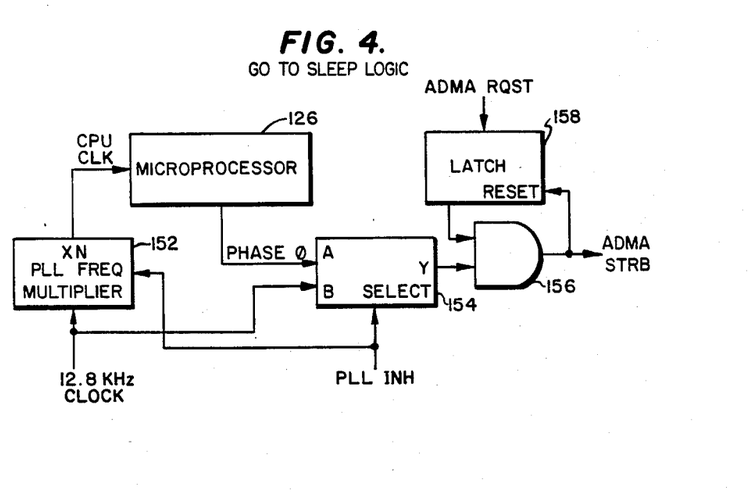
FIG. 4 is the logic diagram for the "go to sleep" logic for the defibrillator.

Generally, microprocessor 126 is put asleep by inhibiting the CPU clock pulses supplied thereto. In FIG. 4, a 12.8 kHz clock pulse is applied to phase lock loop (PLL) frequency multiplier 152 as well as to flip-flop 154 at input B. DMA controller 124 (FIG. 3) includes circuitry to determine whether any events have occurred which require microprocessor 126 to be awakened. In the absence of those predetermined events, DMA controller 124 generates a PLL INH (phase lock loop inhibit) signal which is applied to PLL frequency multiplier 152 in FIG. 4 (see PLL INH to PLL/divider 136 in FIG. 3) and is also applied to the select input of switch 154. The presence of the PLL INH signal inhibits the CPU clock pulses from being applied to microprocessor 126 via PLL frequency multiplier 152. As clearly described in the immediately cited patent application, microprocessor 126 goes to sleep during phase zero of its instruction cycle. That phase is detected at the A input of switch 154. The output of switch 154 is coupled to one input of AND gate 156. The other input of AND gate 156 is coupled to latch 158 which in turn receives the ADMA RQST signal from the shift register in the data compression circuit 20. AND gate 156 generates an ADMA STRB (ADMA strobe) signal which is also fed to the reset input of latch 158. Therefore, the ADMA STRB signal will be generated either synchronously with respect to the 12.8 kHz clock pulse when the microprocessor is asleep or synchronously with respect to the phase zero when the microprocessor is awake.

Returning to FIG. 3, the ADMA STRB signal is applied to the shift register in the data compression circuit 20 which enables the register to place its contents on data bus 120. As is recognized by persons of ordinary skill in the art, the DMA transfer of data over data bus 120 occurs transparently with respect to the operation of microprocessor 126. In this particular embodiment, the DMA transfer of the ECG data into FIFO 146 of RAM 130 occurs during phase zero of the instruction cycle of microprocessor 126 or when the microprocessor is asleep and the address and data busses are in a high impedance state. Substantially simultaneous to the placement of data on the data bus 120 by the shift register, DMA controller 122 generates a DMA EN signal directed to RAM 130 to enable the RAM to accept the byte of ECG data. DMA controller 124 includes an ECG FIFO pointer counter which is incremented on the trailing edge of ADMA STRB to point to the next available location in FIFO 146. This pointer counter is truncated to eight bits so that it wraps around on overflow.

Figures 5A, 5B:
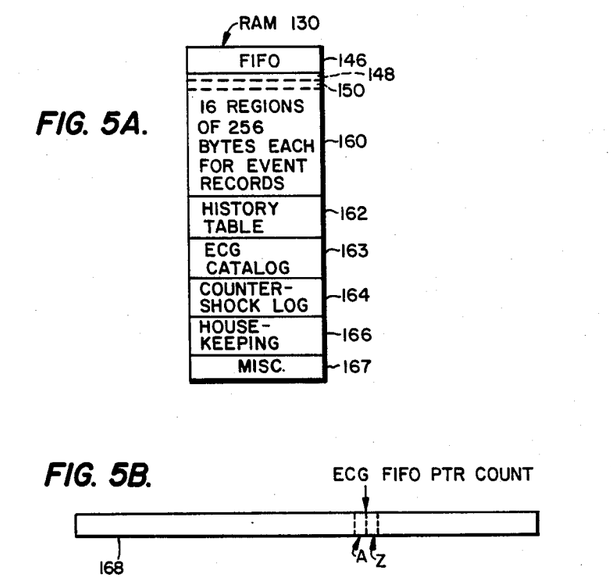
FIG. 5a is a graphic illustration of the RAM partitions.
FIG. 5b is a graphic illustration of the FIFO region in the RAM.

In this embodiment, FIFO 146 holds 256 bytes of ECG data. FIG. 5a presents a functional diagram of RAM 130 showing FIFO 146, section 160 which includes 16 regions of 256 bytes each for the permanent storage or recording of events or patient designated ECG data (which includes regions 148 and 150); history table 162; ECG catalog 163; countershock log 164; housekeeping region 166; and miscellaneous region 167.

FIG. 5b graphically illustrates the FIFO as a longitudinal region 168 wherein each ECG byte of data is stored successively and continuously from left to right. The most recent ECG data is immediately stored in byte A to the left of ECG FIFO Pointer Counter arrow and the oldest ECG data byte Z is located to the right of the ECG FIFO Pointer Counter arrow. As DMA controller 124 enables the shift register by the ADMA STRB signal to place the data on data bus 120 and enables RAM 130 via DMA EN signal to accept that data, the oldest data byte Z is overwritten with the most current detected ECG data byte and ECG FIFO pointer counter is incremented, i.e., the arrow moves to the right. At the right end of the FIFO, the ECG FIFO Pointer Counter is wrapped around and the arrow would be left justified with respect to longitudinal region 167.

When a predetermined cardiac event is indicated by arrhythmia detector 32, an interrupt is generated and sent to interrupt controller 134 which (1) is detected by DMA controller 124 and utilized to wake up microprocessor 126, and (2) is applied to microprocessor 126 in a prioritized fashion by interrupt controller 134 as is well known by persons of ordinary skill in the art. Generally, after suitable identification of the event, microprocessor 126 activates pacer/countershock generator 34 to apply pacing pulses or a countershock to the heart as prescribed by programs stored in ROM 128. After execution of other priority matters, the contents of FIFO 146 will be block transferred or copied under DMA control into one of the 16 regions (e.g., region 148) in section 160 of RAM 130 to preserve a record of the heart's activity prior to and during the application of the prescribed treatment. This DMA transfer between FIFO 146 and one of the 16 regions is substantially similar to the DMA transfer when a patient record command is sent via patient controller 60 to defibrillator 10 which will be described later.

Returning to the operation of the patient commanded ECG recording, after the telemetry mode communications transfer between patient controller 60 and communications section 26 (FIG. 2) and upon sensing the presence of the FSK signal from patient controller 60, communications board 138 generates a carrier detect (CAR DET) interrupt for interrupt controller 134 and the synchronous receiver transmitter SRT 132. The presence of a carrier detect interrupt receives high priority in the interrupt controller 134 and microprocessor 126 is awakened by DMA controller 124 changing the state of PLL INH and by the direct application of CPU clock pulses to microprocessor 126 by PLL/divider 136. Briefly, the line labeled RUN from communications board 138 to PLL/divider 136 and interrupt controller 13 corresponds to clock system run/idle circuit 50 in FIG. 1 and its state determines the run/idle status of the device.

SRT 132 is an 8 bit plus odd parity, half duplex, 400 baud, synchronous serial communications I/B port. It is capable of recognizing and synchronizing to a "sync" carrier ($AA_H$); detecting various error conditions such as overflow, underflow, and parity errors; double buffering the data; and through I/O mapped registers and an error event flag, sending and receiving data and monitoring the status of the SRT and the status of the CAR DET line from communications board 138. As an initial check for the integrity of the data received via the communications link, SRT 132 checks the lateral parity of each received byte.

When a byte is received, a DATA INT (data interrupt) is generated for interrupt controller 134. Microprocessor 126 responds accordingly and processes that received data byte through data bus 120 to various other components. The message body of the transmitted data from the patient controller 60 is set not to exceed 32 bytes in length. After the receipt of the total message from patient controller 60, microprocessor 126 checks the longitudinal parity of the entire message sent from patient controller 60.

The received message is appropriately stored by microprocessor 126 in, e.g., RAM section 167. After microprocessor 126 has confirmed the integrity of the patient ECG record command sent from patient controller 60, a DMA transfer copies the ECG data from FIFO 146 into a particularly designated region of the 16 regions 160 in RAM 130. This DMA transfer is a block transfer of 256 bytes of ECG data occurring in consecutive instruction cycles of the microprocessor. Microprocessor 126 includes a register R0 which is loaded with the base address of the destination while DMA controller 124 contains the ECG FIFO Pointer Counter or source address. Thereafter, the microprocessor and DMA controller 124 cooperate to copy the contents of FIFO 146 into the designated region in RAM 130. In this embodiment, 10.24 seconds of ECG data are permanently stored in RAM 130.

DMA controller 124 makes available a byte of data from FIFO 146 (through a register) to the bus 120 such that microprocessor 126 can copy that data into region 148 and simultaneously increment register R0 such that the next oldest ECG byte of data is copied into region 148. After the DMA transfer or copy operation is complete, DMA controller 12 signifies such completion by changing the state of DMA IN line coupled to microprocessor 126. As is recognized by persons of ordinary skill in the art during this DMA process, the microprocessor program is put "on hold" or suspended, hence, the microprocessor need not store the parameters of the suspended program.

As stated earlier, ECG data is also transferred via DMA controller 124 after the detection of a predetermined cardiac event such as a particular arrhythmia. Microprocessor 126 has set aside certain of the 16 regions in sector 160 (see FIG. 5a) for each unique event, e.g., a patient record event, selected arrhythmias such as ventricular fibrillation, ventricular tachycardia, etc. The programs in ROM 128 executed by microprocessor 126 are designed not to overwrite any unique recorded event stored in the RAM regions.

Additionally, microprocessor 126 places data in an ECG catalog 163 such as: date and time of event; electrode signal levels at the beginning and end of the recording; and reason for the recording. Event history table 162 stores the following data: data and time of the event; current diagnosis of the arrhythmia by microprocessor 126; current mode of treatment. Countershock log 164 includes data such as the energy level of the countershock; the battery current; battery voltage; charge time of the capacitor in the countershock generator; and discharge time of the capacitor. RAM 130 may also include other logs such as the alarm log which keeps track of the date, time and reason for actuation of alarm generator 40.

The ECG data stored in RAM 30 is read out to a physician's console at an appropriate time and place. The physician's console includes substantially all of the items described with respect to patient controller 60, however the physician's console obtains the 400 bps data stream from coherent discriminator 80 and further processes that data to determine the contents of RAM 130. The outbound data transfer from defibrillator 10 is limited to a message body of 256 bytes in length. The data transfer occurs by microprocessor 126 obtaining a byte of data from RAM 130 and placing the byte on data bus 120 and enabling SRT 132. The outbound data transfer is accomplished byte by byte by the microprocessor 126. After the readout of the RAM, the physician can "clear" the memory such that the defibrillator can record and store more events as described above.

The claims appended hereto are meant to encompass all modifications apparent to persons of ordinary skill in the art. One of those modifications is, rather than copying FIFO 146 into region 148 of RAM 130, DMA controller 124 would simply transfer the address of FIFO 146 such that FIFO region 146 would be changed to permanent storage region 148 and another region would be designated as FIFO. Also, the DMA transfer could occur by cycle stealing the instruction cycles from microprocessor 126 rather than operating transparently with respect to the microprocessor as discussed herein. The claims are meant to cover all such modifications.

We claim:

1. An implantable automatic defibrillator capable of recording electric signals indicative of the physiology of a patient's heart upon detection of predetermined events and upon detection of an externally generated patient ECG recording command signal comprising:

an internal means for sensing said electrical signals indicative of the physiology of said patient's heart;

an implantable device receiving said electrical signals including:

means for converting said electrical signal into digital signals representative of said physiology of said patient's heart;

a memory means having a plurality of designated regions, a first region designated to continuously store a first group of digital signals representing the current heart physiology sensed over a recent time period, a second region designated to permanently store a second group of digital signals derived from said first group of digital signals previously stored in said first region;

a direct memory access controller having means for transferring said digital signals on a continuous basis from said means for converting to said first region of said memory means and for updating said first group of digital signals, and having means for copying and permanently storing said first group of digital signals concurrently in said second region of said memory means as said second group of digital signals upon receipt of a transfer command;

means for detecting a plurality of predetermined physiological heart events and for generating an event signal command, the detecting means monitoring said digital signals from said means for converting;

a transmitter means for converting and sending data representative of said second group of digital signals externally outbound from said implantable device;

a receiver means for sensing the presence of said externally generated patient ECG recording command signal and for generating a patient record command;

means for the controlled delivery of electrical pulses to stimulate said patient's heart, based upon said physiology of said patient's heart;

a microprocessor coupled to said memory means, said direct memory access controller, said detecting means, said transmitter means, said receiver means, and said means for delivering, said microprocessor controlling said means for delivering, said microprocessor having:

means for recognizing said patient record command and said event signal command and for generating said transfer command such that said direct memory access controller permanently stores said first group of digital signals in said second region of said memory means as said second group of digital signals; and means for actuating said transmitter means to effect the outbound transmission of data representative of said second group of digital signals.

2. An implantable automatic defibrillator as claimed in claim 1 wherein said microprocessor includes means for assisting said direct memory access controller during the permanent storage of said first group of digital signals into said second region, and includes means for determining the type of predetermined event and means for designating which region of said plurality of regions in said memory means will permanently store said first group of digital signals from said first region.

3. An implantable automatic defibrillator as claimed in claim 2 wherein said microprocessor includes means for overwriting said second group of digital signals in the region designated for one type of predetermined event to store the most recent events or other hierarchy of events.

4. An implantable automatic defibrillator as claimed in claim 3 wherein said first region of said memory means is a FIFO region, and direct memory access controller transfers data into said FIFO region.

5. A patient controlled implantable automatic defibrillator capable of recording electrical signals indicative of the physiology of a patient's heart upon detection of predetermined events and upon actuation by the patient comprising:

a patient actuated controller having:
a patient input means;
means for generating a recording command signal upon actuation of said patient input means; and
means for transmitting said recording command signal;

an implantable device receiving said electrical signals including:

means for sensing said electrical signals indicative of the physiology of said patient's heart;

means for converting said electrical signals into digital signals representative of said physiology of said patient's heart;

a memory means having a plurality of designated regions, a first region designated to continuously store a first group of digital signals representing the current heart physiology sensed over a recent time period, a second region designated to permanently store a second group of digital signals derived from said first group of digital signals previously stored in said first region;

a direct memory access controller having means for transferring said digital signals on a continuous basis from said means for converting to said first region of said memory means and for updating said first group of digital signals, and having means for copying and permanently storing said first group of digital signals concurrently in said second region of said memory means as said second group of digital signals means upon receipt of a transfer command;

means for detecting a plurality of predetermined physiological heart events and for generating an event signal command, the detecting means monitoring said digital signals from said means for converting;

a transmitter means for converting and sending data representative of said second group of digital signals externally outbound from said implantable device;

a receiver means for sensing the presence of said recording command signal and for generating a patient record command;

means for the controlled delivery of electrical pulses to stimulate said patient's heart;

a microprocessor being coupled to said memory means, said direct memory access controller, said detecting means, said transmitter means, said receiver means and said means for delivering, said microprocessor controlling said means for delivering, said microprocessor having:

means for recognizing said patient record command and said event signal command and for generating said transfer command such that said direct memory access controller stores said first group of digital signals in said second region of said memory means as said second group of digital signals; and means for actuating said transmitter means to effect the outbound transmission of data representative of said second group of digital signals.

6. An implantable automatic defibrillator as claimed in claim 5 wherein said recording command signal includes a device code unique to said implantable device, and said microprocessor including means for confirming said device code unique thereto before generating said transfer command.

* * * * *